United States Patent
Wang

(10) Patent No.: US 8,257,576 B2
(45) Date of Patent: Sep. 4, 2012

(54) AMMONIA GAS SENSORS WITH LANTHANIDE VANADATE SENSING ELECTRODE

(75) Inventor: Da Yu Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 232 days.

(21) Appl. No.: 12/840,340

(22) Filed: Jul. 21, 2010

(65) Prior Publication Data

US 2010/0282619 A1    Nov. 11, 2010

Related U.S. Application Data

(63) Continuation-in-part of application No. 11/483,448, filed on Jul. 10, 2006, now Pat. No. 7,828,955, which is a continuation of application No. 10/734,018, filed on Dec. 11, 2003, now Pat. No. 7,074,319.

(60) Provisional application No. 60/432,601, filed on Dec. 11, 2002.

(51) Int. Cl.
*G01N 27/407* (2006.01)
*C25B 11/04* (2006.01)

(52) U.S. Cl. .............. 205/780.5; 204/424; 204/291
(58) Field of Classification Search ............. 205/780.5; 204/424, 291
See application file for complete search history.

(56) References Cited

U.S. PATENT DOCUMENTS

| | | |
|---|---|---|
| 7,074,319 B2 | 7/2006 | Wang et al. |
| 2003/0062264 A1 | 4/2003 | Kitanoya et al. |
| 2004/0118703 A1 | 6/2004 | Wang et al. |
| 2006/0266659 A1 | 11/2006 | Wang et al. |
| 2009/0014330 A1 | 1/2009 | Sugaya et al. |

*Primary Examiner* — Alex Noguerola
(74) *Attorney, Agent, or Firm* — Mark H. Svoboda

(57) ABSTRACT

An ammonia gas sensor is disclosed that includes a reference electrode, an ammonia selective sensing electrode and an electrolyte disposed therebetween. The ammonia sensing electrode comprises an oxide material characterized by the formula $$Ce_wA_xL_yVO_z$$

wherein L is lanthanum or another lanthanide element other than cerium, A is one or more other metals, and w, x, y and z are numbers indicative of atomic proportion with w ranging from about 0.001 to about 4 x ranging from 0 to about 0.8, y ranging from about 0.001 to about 4, and z with a range to balance the existence of Cew, Ax, Ly and V.

20 Claims, 2 Drawing Sheets

AMMONIA GAS SENSORS WITH LANTHANIDE VANADATE SENSING ELECTRODE

CROSS REFERENCE TO RELATED APPLICATIONS

This application is a continuation-in-part of U.S. patent application Ser. No. 11/483,448, filed Jul. 10, 2006, which is a continuation of U.S. patent application Ser. No. 10/734,018, filed Dec. 11, 2003, and claims the benefit of U.S. Provisional Application No. 60/432,601, filed on Dec. 11, 2002, the teachings of which are incorporated herein by reference in their entirety.

BACKGROUND

Exhaust gas generated by combustion of fossil fuels in furnaces, ovens, and engines, for example, contains nitrogen oxides ($NO_x$), unburned hydrocarbons (HC), and carbon monoxide (CO). Automobile gasoline engines utilize various pollution-control after treatment devices such as, for example, a three-way catalyst converter to reduce and oxidize $NO_x$, CO, and HC. The $NO_x$ reduction is accomplished by using ammonia gas ($NH_3$) supplied by a urea tank, or by using HC and CO, which is generated by running the engine temporarily in rich conditions. The overall reaction for converting urea to ammonia is:

$$NH_2CONH_2 + H_2O(\text{steam}) \rightarrow 2NH_3 + CO_2.$$

The product gas is a mixture of ammonia gas, and carbon dioxide ($CO_2$). In order for urea-based catalysts and trap technologies to work efficiently, and to avoid pollution breakthrough, an effective feedback control loop is needed to manage the regeneration cycle of the $NO_x$ traps. To develop such control technology, there is an ongoing need for an economically-produced and reliable commercial ammonia sensor.

A need also exists for a reliable ammonia sensor for air ammonia monitoring in agricultural plants where ammonia present in animal shades, and in all other industries wherein ammonia is produced or used or is a by-product. Commercially available sensors typically suffer from lack of high sensitivity and selectivity. Thus, a widespread need exists for an improved ammonia gas sensor.

SUMMARY

In accordance with an exemplary embodiment of this invention, an ammonia gas sensor comprises an electrolyte, a reference electrode in contact with the electrolyte, and an ammonia selective sensing electrode in contact with the electrolyte spaced apart from the reference electrode. The ammonia selective sensing electrode comprises an oxide material characterized by the formula

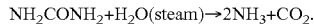

$$Ce_w A_x L_y V O_z \qquad (I)$$

wherein L is lanthanum or another lanthanide element other than cerium, A is one or more other metals, and w, x, y and z are numbers indicative of atomic proportion with w ranging from about 0.001 to about 4, x ranging from 0 to about 0.8, y ranging from about 0.001 to about 4, and $O_z$ is to balance the existence of $Ce_w$, $A_x$, $L_y$ and V.

The electrolyte is composed of a material capable of electrochemical transfer of hydrogen ions and/or oxygen ions. A suitable electrolyte is a zirconia composition. The zirconia composition may contain an additive adapted to stabilize the zirconia at elevated temperatures. In an exemplary embodiment, the electrolyte is yttria-stabilized zirconia.

Referring to the aforementioned formula, A may be one or more dopants to impart desired properties to the oxide material. For example, it may be an additive to enhance electrical conductivity, such as nickel, lithium, zirconium [bismuth, lead, strontium, calcium, copper, lithium, gold, tin, zinc, nickel, titanium, iron, indium, manganese, or magnesium]. Such a conductivity enhancing dopant, if present, may be present in an amount of x between about 0 and 0.8 in one exemplary embodiment, between about 0.01 about 0.6 in another exemplary embodiment, or between about 0.1 and 0.5 in yet another exemplary embodiment. The oxide material may further comprise a chemically stabilizing dopant, such as tantalum, niobium, or magnesium, present in an amount of x between about 0 to about 0.4 in one exemplary embodiment, or between about 0.01 to about 0.3 in another exemplary embodiment. Further, the oxide material may contain a diffusion-impeding dopant, such as zinc, zirconium, lead, iron, or yttrium. As is apparent from this description, some of these dopants impact multiple properties (e.g., zirconium may enhance conductivity and impede diffusion.

In one aspect of this invention, a process for measuring the concentration of ammonia in a gas is provided using an ammonia gas sensor in accordance with the above description. The gas to be measures is contacting with the ammonia selecting sensing electrode; and a voltage signal is measured between said ammonia sensing electrode and said reference electrode.

BRIEF DESCRIPTION OF DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Figure 1:
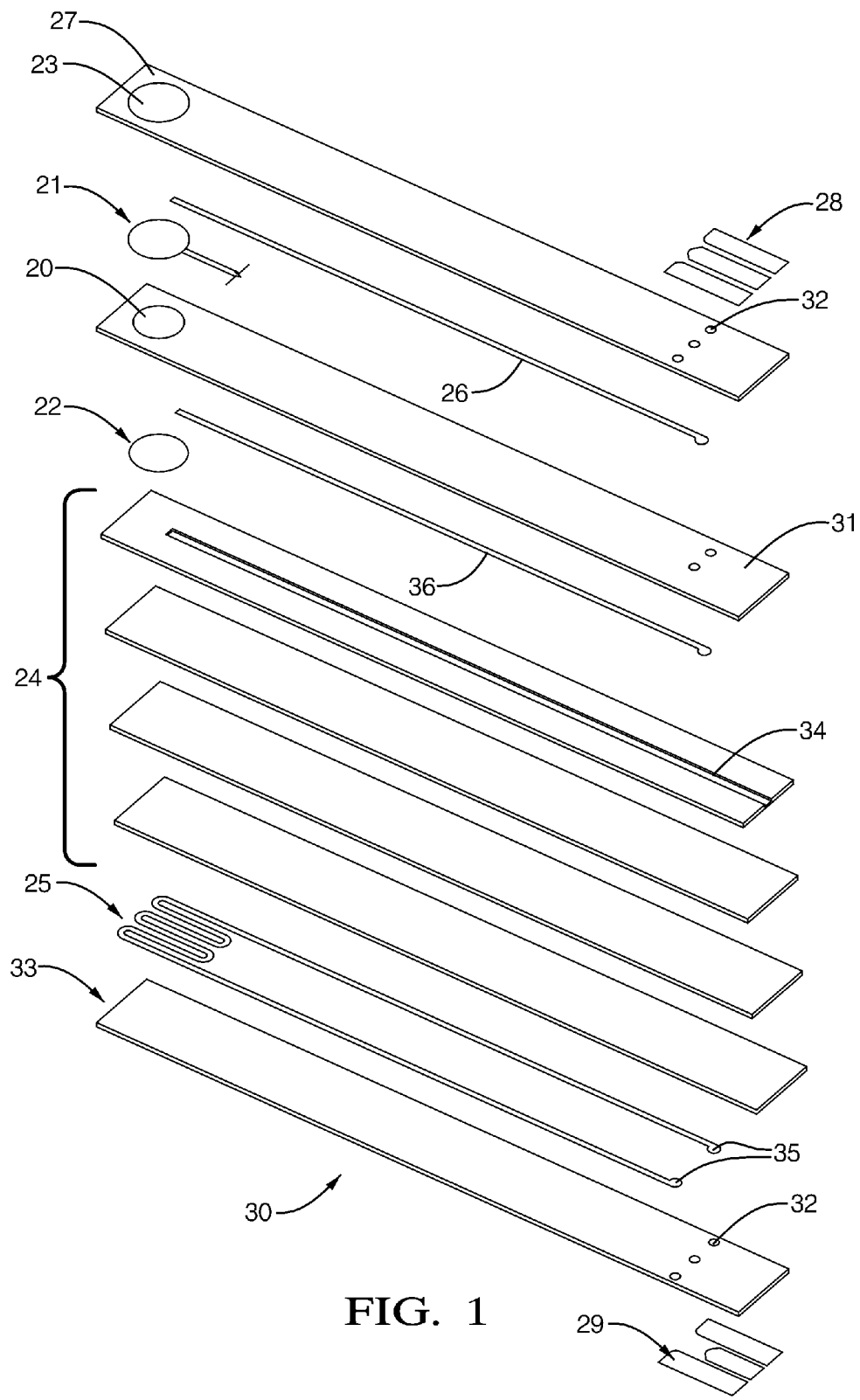
FIG. 1 is a schematic partial cutaway view of an ammonia gas sensor with the layers separated.

The present disclosure relates to an ammonia sensor for monitoring and measuring ammonia gas in a gas stream such as exhaust gases in combustion systems, for example, internal combustion engines and furnaces. It is noted that, although the sensor is described in relation to a flat plate sensor, other sensor designs can also be employed, such as conical and the like.

An ammonia gas sensor may employ a pair of electrodes disposed on opposite sides of an electrolyte (e.g., yttria ($Y_2O_3$) stabilized zirconia ($ZrO_2$)) element. One of the electrodes, referred to herein as a reference electrode, is typically surrounded by a gas having a predetermined ammonia concentration or by ambient air, or by the same gas of which the $NH_3$ amount needs to be sensed. The other electrode, referred to herein as a sensing electrode, is exposed to the gas being monitored or tested for its concentration of ammonia. The gas being tested or monitored is referred to herein as the sensing gas. Therefore, when the concentration of ammonia molecules is greater at one of the electrodes than at the other, an electron imbalance will occur at the respective electrodes, and a voltage is generated between the electrodes. In the case where the reference electrode is also exposed to the sensing gas, the reference electrode comprises materials (e.g., platinum (Pt), and the like) that will catalytically equilibrate the $NH_3$ with the oxygen, leaving no $NH_3$ on the reference electrode electrochemical active area. In such a situation, the $NH_3$ activity difference between the two electrodes will produce the emf. The output voltage is a function of the partial pressures of ammonia in the sensing gas, as well as the temperature of the electrolyte. The voltage generated between the two electrodes is defined by the following equation:

$$E = -\left(\frac{RT}{zF}\right) \times \ln\left(\frac{P_1}{P_2}\right) + C$$

wherein

E=electromotive force;

T=the absolute temperature of the sensor in degrees Kelvin (° K);

R=the Universal Gas Constant=8.3145 Joule per mole·° K (J/(mole·° K));

z is the charge number of the electrode reaction (i.e., the number of moles of electrons involved in the reaction as written);

F=Faraday's Constant=96,500 coulombs/mole;

$P_1$=the partial pressure in atmospheres, of ammonia in the reference gas;

$P_2$=the partial pressure, in atmospheres, of the monitored gas (sensing gas);

C=a constant for each individual sensor; and $$\ln\left(\frac{P_1}{P_2}\right)$$

is the natural logarithm of the ratio $$\left(\frac{P_1}{P_2}\right).$$

The ammonia gas sensor can comprise two electrodes that are used together with an electrolyte. One electrode, the reference electrode, can be exposed to a reference gas, e.g., air ambient air or even the gas to be sensed. The other electrode, the sensing electrode, can be exposed to the gas to be monitored (i.e., the sensing gas), and therefore comprises materials that are selectively sensitive to ammonia and preferably not sensitive to nitrogen oxides ($NO_x$), carbon monoxide (CO), and hydrocarbons (HC), wherein not sensitive means that the sensor output (e.g., millivolts (mV)) in the presence of $NH_3$ is substantially the same in the presence of $NH_3$, NOx, HCs, and CO (i.e., within the level accepted by application). In other words, when a gas comprising 100 ppm $NH_3$ is tested, a sensor reading of 140 mV may be obtained. When the same sensor is used to sense a gas comprising 100 parts per million (ppm) $NH_3$, 1,000 ppm NO, 100 ppm HC, and 100 ppm CO, the sensor output voltage will be about 133 mV to about 147 mV. As used herein, unless otherwise specified, ppm is by weight and based upon the total volume of the gas. Essentially, the difference between the two electrodes causes an electromotive force to be generated when the sensor is placed in a gas stream containing ammonia gas. The resultant electrical potential is a function of the ammonia concentration. As described above, the sensing function is based electrochemical principles.

Referring now to the Figures, where like elements are numbered the same, FIG. 1 shows a schematic cutaway view of a sensor 30 is shown to comprise a sensor protective layer 27 with a porous portion 23, which can allow a sensing gas to diffuse through to reach the outer electrode, and a sensing electrode 21 that is in ionic communication with an electrolyte 20 and electrical communication with vias 32 through sensor lead 26. Sensor protective layer 27 is located between contact pads 28 and sensor lead 26. The sensing electrode 21 can be exposed to the gas to be sensed, e.g., the gas stream or sensing gas. On the side of the sensing electrode 21 opposite the protective layer 27, is an electrolyte layer 31 comprising an electrolyte 20. On the other side of electrolyte 20 is the inner electrode, i.e., a reference electrode 22. On a side of the reference electrode 22, opposite the electrolyte layer 31, is a reference gas channel 34 (and/or a chamber (not shown) for reference gas) in fluid communication with the reference channel. In the case, where the sensing gas is also used as the reference gas, the channel 34 will open (e.g., to the side) to access the sensing gas. Between the reference electrode 22 and the associated reference lead 36 and a heater 25 are one or more insulating layers 24. Optionally, a temperature sensor (not shown) may be disposed between layers 24 for control of the heater 25, and/or a ground plane (not shown) may be disposed therebetween. The heater 25, which is disposed in thermal communication with the sensing end of the sensor (i.e., the end comprising the electrodes 21, 22), is preferably located between the insulating layers 25 and a heater protective layer 33. On the outside of the sensor element 30, on a side of the heater protective layer 33, are contact pads 29 in electrical communication with vias 32 that are in electrical communication with the heater leads 35.

The sensing electrode material described herein includes cerium in an amount of w about 0.001 to about 4 in one exemplary embodiment, about 0.01 to about 3 in another exemplary embodiment, and about 0.1 to about 1 in yet another exemplary embodiment. The material also includes lanthanum or another lanthanide element in an amount of about 0.001 to about 4 in one exemplary embodiment, about 0.01 to about 3 in another exemplary embodiment, and about 0.1 to about 1 in yet another exemplary embodiment.

The sensing electrode material described herein may be used in combination with electrically conductive metals and/or metal oxides. Electrical conducting metals that can be employed comprise Pd, Pt, Au, and the like, as well as alloys and combinations comprising at least one of the foregoing conducting metals, while possible electrical conducting metal oxides comprise oxides of bismuth (Bi), lead (Pb), magnesium (Mg), strontium (Sr), zirconium, calcium (Ca), copper (Cu), lithium, nickel, tin, zinc, indium, gold, iron, others such as BaO, CaO, $Cu_2O$, $Ba_2CaCu_2$ oxide, BiPbSr-CaCu oxide, $Ba_2Cu_3$ oxide, LaSr (Co, Fe, In, Ti, and/or Mn) oxide (e.g., LaSrCu oxide, and the like), LaCo oxide, BiSrFe oxide, and the like.

In one exemplary embodiment, the sensing electrode material in the sensing electrode may be doped with an electrically conductive metal and optionally a chemical stabilizing metal. When the sensing electrode material is doped with the electrically conductive metal, that metal is represented in $A_x$. In such a case, an electrically conductive metal such as bismuth may be present in an amount of x about 0 to about 0.8. In one exemplary embodiment, the x amount of electrically conducting metal is between 0.01 and to about 0.6. In another exemplary embodiment, the x amount of electrically conducting metal is between 0.1 and to about 0.5. When the formulation is further doped with a chemically stabilizing metal(s)/dopant (s) (e.g., tantalum (Ta), niobium (Nb), Mg, and the like, as well as oxides and combinations comprising at least one of these dopants), the chemically stabilizing metal is included in Ax, also included are the diffusion-impeding dopant(s) (e.g., zinc (Zn), iron (Fe), zirconium (Zr), lead (Pb), yttrium (Y), and/or the like, as well as combinations of dopants.

The chemical stabilizing dopant(s), which help to eliminate the green effect, can be present in an amount of x about 0 to about 0.4. Meanwhile, the diffusion impeding dopant(s), which helps to inhibit poisoning of the electrode by contaminants such as Pb, Zr, Zn, Fe, and Y, the chemically stabilizing metal(s) can be collectively present in an amount of x about 0 to about 0.4.

The formulation for the sensing electrode 21 can be formed in advance of deposition onto the electrolyte 20 or can be disposed on the electrolyte 20 and formed during the firing of the sensor. For example, a typical oxygen sensing electrode formulation can be disposed on the electrolyte 20 (the "initial formulation"). A layer (e.g., sprayed, painted, dipped, screen printed, laminated, and/or the like) can be placed over the initial formulation. The layer comprises vanadium oxide, cerium, lanthanum or other lanthanide, any dopants such as conducting metal/oxide (e.g., Bi, Pb, Sr, Ca, Cu Au, In, Zn, Mn, Ti, Sn, and/or the like), chemically stabilizing metal(s) (e.g., Mg, Ta, and/or the like), and/or diffusion-impeding dopants (e.g., Zr, Fe, Zn, Pb, Y, and/or the like) and oxygen, which is typically introduced in the form of oxides of the other materials. When the sensor is fired, these react with each other and with the initial formulation to form a reaction product, the sensing electrode.

To avoid inconsistency (lack of repeatability) of the above process, one may first prepare the sensing formulation and then dispose it onto the electrolyte (or the layer adjacent the electrolyte). In this method, the main material, preferably in the form of an oxide, is combined with the other metals/oxides simultaneously or sequentially. By either method, the materials should be well mixed (e.g., by milling) to enable the desire replacement of the main metal and/or conducting metal in the formulation to produce the desired sensing electrode. The mixture is fired to about 800° C. to about 1400° C. for a sufficient period of time to allow the metals to transfer into the vanadium oxide structure and produce the final formulation, which is the reaction product of the main material, electrically conductive material, chemical stabilizing dopant, and/or diffusion impeding dopant. The period of time is dependent upon the specific temperature and the particular materials, but may be about 0.5 hours to 24 hours or so. Once the sensing formulation has been prepared, it can be made into an ink and disposed onto the desired sensor layer.

If an ink is employed, beside the above metals/oxides/dopants, it may also comprise binder(s), carrier(s), wetting agent(s), and the like, and combinations comprising at least one of the foregoing. The binder may be any material capable of providing adhesion between the ink and the substrate. Suitable binders include acrylic resin, acrylonitrile, styrene, acrylic acid, methacrylic acid, methyl acrylate, methyl methacrylate, and the like, as well as combinations comprising at least one of these binders. The carrier may include any material suitable for imparting desired printing and drying characteristics of the ink. In general, the carrier includes a polymer resin dissolved in a volatile solvent. The wetting agent may include ethanol, isopropyl alcohol, methanol, cetyl alcohol, calcium octoate, zinc octoate and the like, as well as combinations comprising at least one of the foregoing. For example, the ink may comprise about 10 weight percent (wt %) to about 30 wt % 1-methoxy-2-propanol acetate solvent, about 10 wt % to about 30 wt % butyl acetate solvent, about 5 wt % to about 10 wt % acrylic resin binder, 0 to about 5 wt % (e.g., 0.1 wt % to about 5 wt %) methyl methacrylate polymer, about 5 wt % to about 10 wt % ethanol wetting agent, and about 30 wt % to about 60 wt % of the sensing formulation, based upon the total weight of the ink.

In contrast to the sensing electrode 21, the reference electrode 22 can comprise any electrode material, i.e., it does not need to be sensitive to $NH_3$. The reference electrode 22 can comprise any catalyst capable of producing an electromotive force across the electrolyte 20 when the sensing electrode 21 contacts $NH_3$, including metals such as platinum, palladium, gold, osmium, rhodium, iridium, ruthenium, zirconium, yttrium, cerium, calcium, aluminum, and the like, as well as alloys, oxides, and combinations comprising at least one of the foregoing catalysts. A catalyst comprising platinum is preferred due to platinum having a processing temperature as high the ceramic parts (1,400° C. and above), and being readily commercially available as an ink.

Fugitive materials can also be employed in the electrode formulations to enable the desired porosity of the final electrodes, e.g., a sufficient porosity to enable the ammonia to enter the electrode and reach triple points (points where the electrode, electrolyte, and ammonia meet to enable the desired reactions). Fugitive materials, i.e., materials that degrade leave voids upon firing. Some possible fugitive materials include graphite, carbon black, starch, nylon, polystyrene, latex, other soluble organics (e.g., sugars and the like) and the like, as well as compositions comprising one or more of the foregoing fugitive materials.

With respect to the size and geometry of the sensing and reference electrodes 21, 22, they are generally adequate to provide current output sufficient to enable reasonable signal resolution over a wide range of ammonia concentrations. Generally, a thickness of about 1.0 micrometers to about 150 micrometers can be employed, with a thickness of about 5 micrometers to about 100 micrometers preferred, and about 10 micrometers to about 80 micrometers more preferred. The geometry of the electrodes is usually substantially similar to the geometry of the electrolyte.

Electrodes can be formed using techniques such as chemical vapor deposition, screen printing, sputtering, and stenciling, among others, with screen printing the sensing and reference electrodes onto appropriate tapes being preferred due to simplicity, economy, and compatibility with the subsequent firing process. For example, reference electrode 22 can be screen printed onto support layer 24 or over the electrolyte 20, and the sensing electrode 21 can be screen printed under porous protective layer 23 or over the electrolyte 20.

Electrode leads 26, 36 (as well as heater leads) and vias 32 in the layers 27, 31, 33 are typically formed simultaneously with electrodes. However, if the sensor element 30 is not co-fired (i.e., all of the green layers laid up to form the green sensor, and the green sensor then fired to form the final sensor), the vias 32 and leads 26, 36 can be formed separately from the electrodes 21, 22. In this embodiment, when the electrodes 21, 22 comprise material(s) that can not be heated to the sintering temperatures without degrading the electrodes 21, 22, the electrodes 21, 22 can be screen printed onto the sintered layer(s) and then fired at a lower temperature to activate the materials.

Although the porosity of reference electrode 22 is typically sufficient to hold an adequate quantity of ammonia to act as a reference, a space for storing reference ammonia (not shown) can be provided between reference electrode 22 and adjoining support layer 24. This space can be formed by depositing a fugitive material between the reference electrode 22 and the adjacent insulating layer such that upon processing the fugitive material burns out leaving a void. Alternatively, reference electrode 22 can be in fluid communication with a point external to the sensor allowing reference gas access to the reference electrode via a channel 34 in layer.

Disposed between the electrodes 21, 22 is an electrolyte 20, which may be a solid electrolyte that can comprise the entire layer 31 or a portion thereof The electrolyte 20 can be any material that is capable of permitting the electrochemical transfer of hydrogen ions and/or oxygen ions while inhibiting the physical passage of exhaust gases, has an ionic/total conductivity ratio of approximately unity, and is compatible with the environment in which sensor element will be utilized (e.g., up to about 1,000° C.). Possible electrolyte materials can comprise metal oxides such as zirconia, and the like, which may optionally be stabilized with calcium, barium, yttrium, magnesium, aluminum, lanthanum, cesium, gadolinium, and the like, and oxides thereof, as well as combinations comprising at least one of the foregoing electrolyte materials. For example, the electrolyte can be alumina and yttrium stabilized zirconia. Typically, the electrolyte has a thickness of up to about 500 micrometers, with a thickness of approximately 25 micrometers to about 500 micrometers preferred, and a thickness of about 50 micrometers to about 200 micrometers especially preferred for planar sensors.

Electrolytes 20 can be formed via many processes including, but not limited to, slurry doctor blade, die pressing, roll compaction, stenciling, and screen printing, and the like. For improved process compatibility, it is preferred to utilize a tape process using known ceramic tape casting methods. If the electrolyte 20 comprises a portion of the electrolyte layer 31, a stamping method may also be employed where the electrolyte is disposed into an opening in the electrolyte layer 31 or attached onto an end of the electrolyte layer 31.

Disposed on a side of the reference electrode 22, opposite the electrolyte 20, can be one or more insulating layers 24, (e.g., dielectric layers), a heater protective layer 33, and a sensor protective layer 27. These layers comprise materials that effectively protect various portions of the sensor element 30, provide structural integrity, and separate various components. Heater protective layer 33 electrically isolates the heater 25 from the sensor circuits, while support layers 24 physically separate the reference electrode 22 and heater 25, and the sensor protective layer 27 protects the sensor 21 and sensor lead 26 from abrasion and contaminants, and provides electrical insulation. These layers may comprise alumina or similar insulating materials that are compatible with the electrolyte and the operating environment, and which are chosen to at least minimize, if not eliminate, delamination and other processing problems.

The insulating layers 24 and protective layers 27, 33, can each be up to about 200 micrometers thick or so, depending upon the number of layers employed, with a thickness of about 50 micrometers to about 200 micrometers preferred. As with the electrolyte layer 31, these layers can be formed using ceramic tape casting methods or other methods such as plasma spray deposition techniques, screen printing, stenciling and others.

The protective layer 27 can comprise a porous portion 23 that has a sufficient porosity to allow the ammonia to pass therethrough, while protecting the electrode from abrasion, particulates, and the like. Possible materials for the porous portion include aluminum oxides, magnesium aluminate, spinel, and the like, as well as combinations comprising at least one of the foregoing materials.

Disposed between the insulating layers 24 and the heater protective layer 33, is the heater 25, with a ground plane (not shown) and/or a temperature sensor (not shown) optionally disposed between two other substrate layers. The heater 25 can be any heater capable of maintaining a sensor end of sensor element 30 at a sufficient temperature to facilitate the various electrochemical reactions therein. The heater, which can be platinum, palladium, aluminum, and the like, or alloys or combinations comprising at least one of the foregoing, or any other heater compatible with the environment, is generally screen printed onto a substrate to a thickness of about 5 micrometers to about 50 micrometers or so.

Leads 26, 35, 36 are disposed across various dielectric layers to electrically connect the external wiring of sensor element 30 with electrodes 21, 22. Leads are typically formed on the same layer as the electrode and heater to which they are in electrical communication and extend from the electrode/heater to the terminal end of the element (i.e., the end opposite the sensing end) where they are in electrical communication with the corresponding via 32.

At terminal end of sensor element, vias 32 are formed as holes filled with electrically conductive material in the appropriate layers or can be a hole at the end of the layer providing electrical communication through the layer. Vias are typically filled during formation of electrodes/heater 21, 22, 25 and leads 26, 35, 36, and serve to provide a mechanism for electrically connecting leads 25, 35, 36 to contact pads 28, 29 on the exterior of sensor element 30. These contact pads 28, 29 provide a contact point for the external sensor circuit.

The disclosed sensors can be built by bulk ceramic technology, or thick-film multi-layer technology, or thin-film multi-layer technology. In bulk ceramic technology, the sensors are formed in a cup shape by traditional ceramic processing methods with the electrodes deposed by ink methods (e.g., screen printing) and/or plasma method. During formation, essentially, the respective electrodes, leads, heater(s), optional ground plane(s), optional temperature sensor(s), optional fugitive material(s), vias, and the like, are disposed onto the appropriate layers. The layers are laid-up accordingly (e.g., as illustrated in FIG. 1), and then fired at temperatures of about 1,400° C. to about 1,500° C. Alternatively, the electrodes are not disposed onto the layers. The green layers (including the leads, optional ground plane(s), optional temperature sensor(s), optional fugitive material(s), vias, and the like) are fired at temperatures sufficient to sinter the layers, e.g., temperatures of about 1,400° C. to about 1,500° C. The electrodes are then disposed on the appropriate fired layer(s), and the layers are laid-up accordingly. The sensor element is then again fired at a temperature sufficient to activate the electrode materials, e.g., temperatures of about 700° C. to about 850° C.

Figure 2:
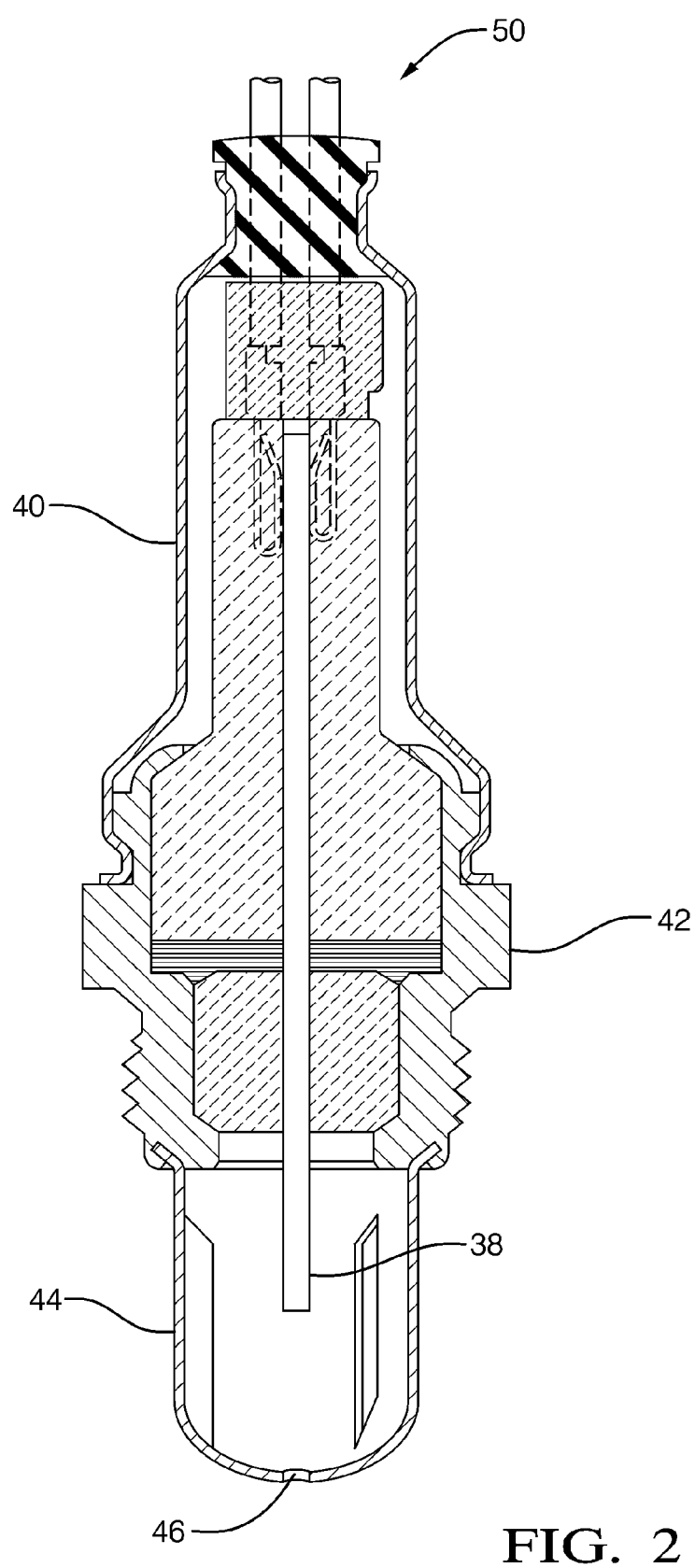
FIG. 2 is a cutaway view of an ammonia gas sensor package comprising sensor 10.

Referring now to FIG. 2, the sintered sensor element 38 is disposed in a housing or package to form the completed sensor 50. The sensor 50 comprises a the sintered sensor element 38, an upper shell 40, a lower shell 42, and a lower shield 44. The sensor element 38 extends from the upper shell 40, through the lower shell 42, and into the lower shield 44. The lower shield 44 has opening(s) 46 to enable fluid communication between the sensing end of the sensor element 38 and the gas to be sensed. To provide structural integrity to the sensor element 38, insulators 62 (e.g., ceramic, talc, mesh (metal or other), and/or the like) are disposed between the sensor element 38 and the shell 40, 42. The terminal end of the sensor 38 is disposed within upper shell 40 in electrical commutation with a terminal interface 48 such that cables 52 can be disposed in electrical communication with the sensor 38 via the contact pads.

During operation, the ammonia sensor is disposed in an area where a gas is to be sensed (e.g., within an exhaust conduit of a vehicle). When a gas passes down the conduit, the gas enters the sensor 50 through opening 46 and contacts the sensor element 38. The gases pass through the porous protective layer 23 where they contact the sensing electrode. Due to the ammonia concentration at the sensing electrode 21 and the insensitivity to the ammonia at the reference electrode 22, ammonia concentration is detected in the gas stream. This information can be fed to an analyzer that is in operable communication with the vehicle. Based upon the ammonia concentration, the introduction of ammonia, urea, and/or the air to fuel ratio of the exhaust stream can be adjusted to attain the desired emissions.

The following examples are intended to further describe the ammonia sensor and electrodes thereof and not to limit the present disclosure.

EXAMPLES

Examples 1-2 illustrate one type of ammonia selective sensing electrode comprising ammonia sensing material in contact with zirconia electrolyte on one hand and also in contact with electrical conducting metal (Pt) printed on electrical inert layer (alumina) on the other hand. The reference electrode (Pt) was printed on the other side of the zirconia electrolyte. Both ammonia sensing electrode and the reference electrode were exposed to testing gas mixture which is composed of ammonia gas and 14% oxygen, 1.5% H2O and balanced nitrogen gas. The testing device was composed of (other than ammonia sensing electrode and the reference electrode) a temperature sensor, a Pt heater. The testing devices were made of thick-film ceramic technology. The testing devices were tested at around 570-620 C. The ammonia sensing emf was measured between the ammonia sensing electrode and the reference electrode.

Example 1

Respective amounts of $CeO_2$, $La_2O_3$ and $V_2O_5$ were weighed according to provide cerium, lanthanum, and vanadium in the relative amounts to the formula of $Ce_{0.2}La_{0.8}VO_4$, mixed and fired in air at 900° C. for 12 hours. After that, the powder was ground and mixed with carbon black and toluene to form an ink. The ink was printed on testing devices and fired in air at 800° C. for one hour. The emf values measured were as follows: 157 mV at 100 PPM of $NH_3$, 69 mV at 1000 ppm of NO, 69 mV at 1000 ppm of $C_6H_6$, and 27 mV at 1000 ppm of CO.

Example 2

Respective amounts of $CeO_2$, $La_2O_3$ and $V_2O_5$ were weighed according to provide cerium, lanthanum, and vanadium in the relative amounts to the formula of $Ce_{0.5}La_{0.5}VO_4$, mixed and fired in air at 900° C. for 12 hours. After that, the powder was ground and mixed with carbon black and toluene to form an ink. The ink was printed on testing devices and fired in air at 800° C. for one hour. The emf values measured were as follows: 141 mV at 100 PPM of $NH_3$, 64 mV at 1000 ppm of NO, 38 mV at 1000 ppm of $C_6H_6$, and 20 mV at 1000 ppm of CO.

In prior methods for monitoring ammonia gas, such as those based on optical principles, problems exist with humidity, high temperature, slow response time, aging effect, CO and hydrocarbon interference effect, manufacturing difficulties, and high cost. The disclosed ammonia gas sensor is reliable for monitoring ammonia concentrations of about 1 ppm to about 100 ppm and above. It operates reliably in concentrations of water vapor of about 0.5 vol % to 12 vol %. It is economically-produced and operated. The disclosed sensor is characterized by quick response time (e.g., less than or equal to about 1 second), and operates over a wide range of temperatures (e.g., temperatures of about 140° C. to about 700° C.).

The present ammonia gas sensor provides many advantages. The electrodes are selectively sensitive to ammonia, and therefore can accurately determine ammonia concentration in an exhaust gas. The sensor is economical to manufacture and to operate. Due to the combination of materials in the sensing formulation, the sensor resists the green effect (i.e., maintains a mV reading, through the first 100 hours of operation, that varies by ±5%), and is resistant to poisoning from the materials of the electrode, as well as air borne contaminants. Additionally, it is easily portable and can be used for pollution monitoring and control in ambient air, indoors or outdoors, in engine exhaust systems, in combustor flues, and elsewhere.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:
1. An ammonia gas sensor, comprising:
an electrolyte;
a reference electrode in contact with the electrolyte; and
an ammonia selective sensing electrode in contact with the electrolyte spaced apart from the reference electrode, said ammonia selective sensing electrode comprising an oxide material characterized by the formula

$$Ce_w A_x L_y VO_z$$

wherein L is lanthanum or another lanthanide element other than cerium, A is one or more other metals, and w, x, y and z are numbers indicative of atomic proportion with w ranging from about 0.001 to about 4, x ranging from 0 to about 0.8, y ranging from about 0.001 to about 4, and z with a range to balance the existence of $Ce_w$, $A_x$, $L_y$, and V.

2. The ammonia gas sensor in accordance with claim 1, wherein the electrolyte comprises a material capable of electrochemical transfer of hydrogen ions, oxygen ions, or both hydrogen and oxygen ions.

3. The ammonia gas sensor in accordance with claim 2, wherein the electrolyte is a zirconia composition.

4. The ammonia gas sensor in accordance with claim 3, wherein the zirconia composition comprises zirconia containing an additive adapted to stabilize the zirconia at elevated temperatures.

5. The ammonia gas sensor in accordance with claim 4, wherein the electrolyte is yttria-stabilized zirconia.

6. The ammonia gas sensor in accordance with claim 1, wherein A includes a conductivity-enhancing metal selected from the group consisting of bismuth, lead, strontium, calcium, copper, gold, zinc, nickel, tin, titanium, iron, lithium, manganese, and magnesium.

7. The ammonia gas sensor of claim 6, wherein the conductivity enhancing metal is present in $A_x$ with an amount of x between about 0 and about 0.8.

8. The ammonia gas sensor of claim 6, wherein the conductivity enhancing metal is present in an amount of x between about 0.01 and 0.6.

9. The ammonia gas sensor of claim 6, wherein the conductivity enhancing metal is present in an amount of x between about 0.1 and about 0.5.

10. The ammonia gas sensor in accordance with claim 1, wherein A includes a chemically stabilizing dopant.

11. The ammonia gas sensor in accordance with claim 10, wherein the chemically stabilizing dopant is selected from the group consisting of tantalum, niobium, and magnesium.

12. The ammonia gas sensor in accordance with claim 10, wherein the chemically stabilizing dopant is present in $A_x$ with an amount of x between about 0 and about 0.4.

13. The ammonia gas sensor in accordance with claim 10, wherein the chemically stabilizing dopant is present in $A_x$ with an amount of x between about 0.01 and about 0.3.

14. The ammonia gas sensor in accordance with claim 1, wherein A includes a diffusion-impeding dopant.

15. The ammonia gas sensor in accordance with claim 14, wherein the diffusion-impeding dopant is selected from the group consisting of zinc, zirconium, lead, iron, and yttrium.

16. The ammonia gas sensor in accordance with claim 1, wherein L is lanthanum.

17. A process for measuring the concentration of ammonia in a gas, the process comprising
providing an ammonia gas sensor comprising an electrolyte, a reference electrode in contact with the electrolyte; and an ammonia selective sensing electrode in contact with the electrolyte spaced apart from the reference electrode, said ammonia selective sensing electrode comprising an oxide material characterized by the formula $$Ce_w A_x L_y VO_z$$

wherein L is lanthanum or another lanthanide element other than cerium, A is one or more other metals, and w, x, y and z are numbers indicative of atomic proportion with w ranging from about 0.001 to about 4, x ranging from 0 to about 0.8, y ranging from about 0.001 to about 4, and z with a ranging to balance $Ce_w$, $A_x$, $L_y$, and V,
contacting the gas with the ammonia selecting sensing electrode; and
measuring a voltage signal between said ammonia sensing electrode and said reference electrode.

18. The process in accordance with claim 17, wherein A includes a conductivity-enhancing metal selected from the group consisting of bismuth, lead, gold, indium, tin, zinc, nickel, lithium, iron, titanium, strontium, calcium, copper, and magnesium.

19. The process in accordance with claim 18, wherein the conductivity-enhancing metal is present in $A_x$ with an amount of x between about 0 to about 0.8.

20. The process in accordance with claim 17, wherein L is lanthanum.

* * * * *